United States Patent [19]

Wolfram et al.

[11] Patent Number: 4,599,435
[45] Date of Patent: Jul. 8, 1986

[54] PREPARATION OF 6-CARBOXY-3,4-DIHYDRO-2H-PYRAN

[75] Inventors: Joachim W. Wolfram; John Y. Lee, both of Baton Rouge, La.

[73] Assignee: Ethyl Corporation, Richmond, Va.

[21] Appl. No.: 715,768

[22] Filed: Mar. 25, 1985

Related U.S. Application Data

[63] Continuation of Ser. No. 544,399, Oct. 21, 1983, abandoned, which is a continuation-in-part of Ser. No. 419,758, Sep. 20, 1982, abandoned.

[51] Int. Cl.$^4$ .......................................... C07D 309/22
[52] U.S. Cl. .......................................................... 549/425
[58] Field of Search ........................................ 549/425

[56] References Cited

U.S. PATENT DOCUMENTS

| | | | |
|---|---|---|---|
| 3,523,952 | 8/1970 | Orth et al. | 548/561 |
| 3,882,146 | 5/1975 | Wiegand | 548/561 |
| 4,120,874 | 10/1978 | Crutchfield et al. | 549/425 |
| 4,374,256 | 2/1983 | Kao et al. | 548/561 |

OTHER PUBLICATIONS

*The Carbonylation of Phase-Transfer Agents*, Gambarotta, et al., *J. of Organometallic Chem.*, 194, C19–C21 (1980).
*Sunlamp-Irradiated Phase-Transfer Catalysis*, 1, Brunet et al., *J. Org. Chem.*, 48, pp. 1166–1171 (1983).
*Sunlamp-Irradiated Phase-Transfer Catalysis*, 2, Brunet et al., *J. Org. Chem.*, 48, pp. 1919–1921 (1983).
*Methyl Transfer to Nucleophilic Metal Carbonylate Anions in Catalytic Methanol Homologation*, Roth et al., *Organometallics*, 3, pp. 708–714 (1984).
*Phase-Transfer Catalysis in Cobalt Catalyzed Carbonylation of Secondary Benzyl Halides*, Francalanci et al., *J. of Electroanalytical Chem.*, 232, (1982), pp. 59–70.
Riobe et al., C. R. Acad. Sc. Paris Series C, 272, 1045–1048 (1971).
LeBouc et al., Synthesis, 610–613 (1979).
Herz et al., JACS, 73, 4921 (1951).
Herz, JACS, 75, 483 (1953).
Carson et al., J. Org. Chem., 42, 1096 (1977).
Jerry March, "Advanced Organic Chemistry: Reactions, Mechanisms, and Structure", pp. 290–294 (1968).

*Primary Examiner*—Nicky Chan
*Attorney, Agent, or Firm*—Donald L. Johnson; John F. Sieberth; W. G. Montgomery

[57] ABSTRACT

6-Carboxy-3,4-dihydro-2H-pyran and ring-substituted derivatives thereof are prepared by reacting a 1,4-disubstituted butane having leaving groups at the one and four positions in a liquid solvent medium with carbon monoxide at elevated temperature and pressure in the presence of a catalytic amount of a metal carbonyl compound and an alkali metal inorganic base or an alkaline earth metal inorganic base.

21 Claims, No Drawings

PREPARATION OF 6-CARBOXY-3,4-DIHYDRO-2H-PYRAN

CROSS-REFERENCE TO RELATED APPLICATION

This application is a continuation of application Ser. No. 544,399, filed Oct. 21, 1983, now abandoned which is a continuation-in-part of Ser. No. 419,758, filed Sept. 20, 1982 now abandoned.

TECHNICAL FIELD

This invention relates to 6-carboxy-3,4-dihydro-2H-pyran and novel ring-substituted derivatives thereof. Further, the invention relates to processes for preparing same.

The practical value of such acids is that they can be used in the synthesis of pharmaceuticals, specialty chemicals and for preparing polymers.

BACKGROUND

The preparation of 6-carboxy-3,4-dihydro-2H-pyran and derivatives of 6-carboxy-3,4-dihydro-2H-pyran has been the subject of a number of investigations.

For example, it is reported by Riobe et al., in *C.R. Acad. Sc. Paris Series C,* 272, 1045–1048, 1971, that 2,3-dichlorotetrahydropyran can be treated with $Cu_2(CN)_2$ in the absence of a solvent to give 2-cyano-3-chlorotetrahydropyran which can be converted to 6-cyano-2H-dihydropyran by subsequent treatment with triethylamine. The 6-cyano-2H-dihydropyran product is then converted to 6-carboxy-3,4-dihydro-2H-pyran by hydrolysis with base. Also, Labouc et al., *Synthesis,* 610–613, 1979, report that 6-lithio-3,4-dihydro-2H-pyrans can be treated with carbon dioxide to form minor amounts of 6-carboxy-3,4-dihydro-2H-pyran.

THE INVENTION

It has now been found that 6-carboxy-3,4-dihydro-2H-pyran and certain novel ring-substituted derivatives thereof corresponding to the formula:

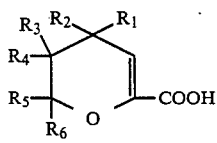

wherein $R_1$, $R_2$, $R_3$, $R_4$ and $R_5$ are the same or different and are hydrogen or linear or branched alkyl, aralkyl or aryl radicals having up to 20 carbon atoms and where $R_6$ is hydrogen, can be prepared by carbonylating a 1,4-disubstituted butane having leaving groups at the one and four positions corresponding to the formula:

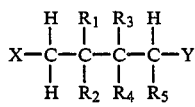

wherein $R_1$, $R_2$, $R_3$, $R_4$ and $R_5$ are as defined above and X and Y are the same or different and are leaving groups, inert to solvolysis under the reaction conditions, in a liquid solvent medium, with carbon monoxide at a pressure of from about 300 to about 3000 psig in the presence of a catalytic amount of a metal carbonyl compound and an alkali metal inorganic base or an alkaline earth metal inorganic base. Exemplary leaving groups, X and Y, include halo (e.g., bromine chlorine or iodine), sulfonate (e.g., tosylate) and tertiary amines.

The 1,4-disubstituted butane reactants suitable for use in the present process are known in the art as are methods for their preparation and, as defined above, are of the general formula:

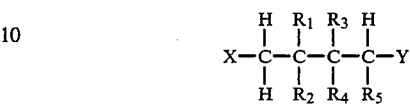

wherein $R_1$, $R_2$, $R_3$, $R_4$, $R_5$, X and Y are as defined above.

A few examplary materials of this type include:
1,4-dibromobutane,
1,4-dibromopentane,
1,4-dibromo-3-methylbutane,
1,4-dibromo-2-methylbutane,
1,4-dibromo-3,3-dimethylbutane,
1,4-dibromo-2,2-dimethylbutane,
1,4-dibromo-3-methylpentane,
1,4-dibromo-2,3-dimethylbutane,
1,4-dibromo-2,3-dimethylpentane,
1,4-dibromo-2-(4'-ethylphenyl)butane,
1,4-dibromo-2-(4'-isopropylphenyl)butane,
1,4-dibromo-3-phenyl-butane,
1,4-dibromo-2-phenyl-butane, and
4-bromobutyl-1-p-toluene sulfonate.

A particularly useful reactant is 1,4-dibromobutane.

Products which can be made by the process of the present invention include, by way of example:
6-carboxy-3,4-dihydro-2H-pyran,
6-carboxy-2-methyl-3,4-dihydro-2H-pyran,
6-carboxy-3-methyl-3,4-dihydro-2H-pyran,
6-carboxy-4-methyl-3,4-dihydro-2H-pyran,
6-carboxy-3,3-dimethyl-3,4-dihydro-2H-pyran,
6-carboxy-4,4-dimethyl-3,4-dihydro-2H-pyran,
6-carboxy-2,3-dimethyl-3,4-dihydro-2H-pyran,
6-carboxy-3,4-dimethyl-3,4-dihydro-2H-pyran,
6-carboxy-2,3,4-trimethyl-3,4-dihydro-2H-pyran,
6-carboxy-4-(4'-ethylphenyl)-3,4-dihydro-2H-pyran,
6-carboxy-4-(4'-isopropylphenyl)-3,4-dihydro-2H-pyran,
6-carboxy-3-phenyl-3,4-dihydro-2H-pyran, and
6-carboxy-4-phenyl-3,4-dihydro-2H-pyran.

The reaction is carried out in the presence of a mixture of water and alcohol as a reaction medium. Preferably, the alcohols employed for the reaction may be straight-chain, branched or cyclic, and preferably contain up to 6 carbon atoms. Methanol, ethanol, propanol, isopropanol, n-butanol, isobutanol, tert-butanol, and tert-amyl alcohol may be mentioned as examples. Cyclic ethers, such as tetrahydrofuran, also may be used. A particularly preferred solvent alcohol is tert-butanol. Mixtures containing about 10% to 90% by weight of water and about 90% to 10% by weight of alcohol generally are used. Preferred mixtures contain about 30% to 80% by weight water and about 70% to 20% by weight alcohol.

The reaction takes place in the presence of a basic substance, suitably an alkali metal hydroxide or an alkaline earth metal hydroxide, employing a metal carbonyl compound. During the reaction, the 1,4-disubstituted butane reactant undergoes reaction with the carbon monoxide and basic substance whereby 6-carboxy-3,4- dihydro-2H-pyran or the desired derivatives thereof are formed.

Specific examples of suitable basic agents which can be used in the practice of the process include: LiOH, NaOH, KOH, RbOH, Ca(OH)$_2$, Ba(OH)$_2$ and Mg(OH)$_2$. LiOH and Ca(OH)$_2$ are particularly preferred.

The amount of basic agent used can vary within wide limits. In general, the molar ratio of the alkali metal base or alkaline earth metal base to 1,4-disubstituted butane reactant is preferably 10:1 to 1:1.

In the process described herein, it is preferred to use metal carbonyl compounds as carbonylation catalysts. These catalysts include particularly metal carbonyls such as iron pentacarbonyl, dicobalt-octacarbonyl and nickel-tetracarbonyl, or their salts such as, for example, the calcium, potassium or sodium salts thereof. Dicobalt-octacarbonyl is very particularly suited. These catalysts can be added to the medium in the solid state or in the form of solutions in the solvent used for the carbonylation reaction. The molar percentage of the metal carbonyl compound to the 1,4-disubstituted butane reactant is preferably from about 0.1 to about 25%.

The concentration of the 1,4-disubstituted butane used in the reaction solvent is not critical and can vary within wide limits. Thus, it can be between about 1 and 30% by weight, based on the weight of the solvent, however, it is possible to go outside of these limits without disadvantage.

The present process is advantageously carried out by bringing the mixture consisting of the 1,4-disubstituted butane reactant, the metal carbonyl catalyst and the alkali metal base or alkaline earth metal base, suspended in the mixture of water and alcohol, into contact, under nitrogen, in a suitable pressure-resistant reactor equipped with a stirrer, with a large excess of carbon monoxide (amount greater than 2 moles of carbon monoxide per mole of the starting 1,4-disubstituted butane reactant) introduced at the desired pressure and temperature, in accordance with techniques suitable for bringing about the reaction between a liquid phase and a gas phase.

The carbonylation reaction is carried out at a temperature in the range of from about 30° C. to about 150° C., preferably from about 50° C. to 100° C., over a period of time of from about 3 to 60 hours, typically 3 to 20 hours.

In general, the reaction takes place at elevated carbon monoxide pressures which may range from about 300 psig to about 3000 psig. Preferably, the reaction takes place at a pressure in the range of about 500 psig to 1000 psig. The carbon monoxide may contain or be mixed with an inert gas, such as nitrogen.

On completion of the reaction, the product mixture is filtered, resulting in the alkali metal basic reagent or the alkaline earth metal basic reagent being separated from the liquid reaction components as the main solid component. The desired 6-carboxy-3,4-dihydro-2H-pyran product is easily separated from the resultant reaction mixture by such means as distillation, extraction, crystallization or the like.

Since the derivatives of 6-carboxy-3,4-dihydro-2H-pyran defined above are believed to be novel compounds, in a further embodiment of the present invention, there is provided, as new compositions of matter, compounds of the general formula:

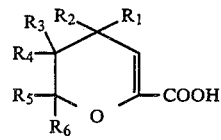

wherein $R_1$, $R_2$, $R_3$, $R_4$ and $R_5$ are the same or different and are hydrogen or linear or branched alkyl, aralkyl or aryl radicals having up to 20 carbon atoms with the proviso that at least one of $R_1$, $R_2$, $R_3$, $R_4$ or $R_5$ must be other than hydrogen and $R_6$ is hydrogen.

The following examples illustrate the invention.

EXAMPLE 1

Into a 300 mL autoclave were charged 9.02 g (52.0 mmoles) of 1-chloro-4-bromobutane and 70 mL of t-BuOH. Next, 0.9 g (2.76 mmoles) of Co$_2$(CO)$_8$ were added under CO, and then a mixture of 15.4 g (approximately 200 mmoles) of lime and 30 mL of H$_2$O were added. After 850 psi CO was charged to the autoclave, the reaction mixture was heated to 90° C. over a period of time of approximately 1 hour and held at that temperature for 15 hours. The CO uptake stopped after approximately 7 hours. After centrifugation, the solid was rinsed once with a 20 mL portion of a 50:50 t-butanol/water solution and then acidified with 150 mLs of HCl solution containing approximately 450 mmoles of HCl. The free acid was extracted from the aqueous solution with diethyl ether (2×120 mLs) to give a 1.12 g (19% yield) of 6-carboxy-3,4-dihydro-2H-pyran based on proton NMR data with internal standard. The filtrate was extracted with 50 mLs of diethyl ether and the extract discarded. The residual aqueous solution was acidified with 10% HCl and extracted with diethyl ether (3×50 mLs). After drying over MgSO$_4$ and evaporation of solvent, a second crop of 6-carboxy-3,4-dihydro-2H-pyran was obtained (3.16 g; 54% yield) for a combined yield of 4.28 g of 6-carboxy-3,4-dihydro-2H-pyran (73% yield).

EXAMPLE 2

Into a 300 mL autoclave were charged 8.83 g (40.93 mmoles) of 1,4-dibromobutane and 70 mLs of t-BuOH. Next, 0.7 g (2.05 mmoles) of Co$_2$(CO)$_8$ were added under CO, and then a mixture of 12.11 g (163.7 mmoles) of lime and 30 mLs of H$_2$O were added. After 850 psi CO was charged to the autoclave, the reaction mixture was heated to 90° C. over a period of time of approximately 1 hour and held at that temperature for 15 hours. The CO uptake stopped after approximately 11 hours. After centriguation, the solid was rinsed once with a 20 mL portion of a 50:50 t-butanol/water solution and then acidified with 150 mL of HCl solution containing approximately 350 mmoles of HCl. The free acid was extracted from the aqueous solution with diethyl ether (2×120 mLs) to give 0.21 g (41% yield) of 6-carboxy-3,4-dihydro-2H-pyran based on proton NLR data with internal standard. The filtrate was extracted with 50 mLs of diethyl ether and the extract discarded. The residual aqueous solution was acidified with 10% HCl and extracted with diethyl ether (3×50 mLs). After drying over MgSO$_4$ and evaporation of solvent, a second crop of 6-carboxy-3,4-dihyro-2H-pyran was obtained (3.45 g; 67.6% yield) for a combined yield of 3.66 g or 71.7% of 6-carboxy-3,4-dihydro-2H-pyran.

Having described the process which Applicant regards as his invention, it should be recognized that changes and variations within the scope and spirit of the invention can be made by one skilled in the art and it is accordingly to be understood that the present description of the invention is illustrative only. It is desired that the invention be limited only by the lawful scope of the following claims.

We claim:

1. A process for preparing 6-carboxy-3,4-dihydro-2H-pyrans corresponding to the formula:

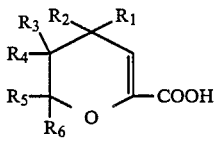

wherein $R_1$, $R_2$, $R_3$, $R_4$ and $R_5$ are the same or different and are hydrogen or linear or branched alkyl, aralkyl or aryl radicals having up to 20 carbon atoms and $R_6$ is hydrogen which comprises reacting 1,4-disubstituted butane having leaving groups selected from halo, sulfonate, and tertiary amines at the one and four positions corresponding to the formula:

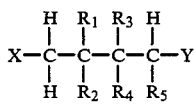

wherein $R_1$, $R_2$, $R_3$, $R_4$ and $R_5$ are as defined above and X and Y are leaving groups which can be the same or different in a liquid solvent medium with carbon monoxide at elevated temperature and pressure in the presence of a catalytic amount of a metal carbonyl compound and an alkali metal inorganic base or an alkaline earth metal inorganic base.

2. The process of claim 1 wherein the leaving group is halogen.

3. The process of claim 2 wherein the leaving group is bromine, chlorine or iodine.

4. The process of claim 1 wherein said 1,4-disubstituted butane is 1,4-dibromobutane, 1,4-dibromopentane, 1,4-dibromo-3-methylbutane, 1,4-dibromo-2-methylbutane, 1,4-dibromo-3,3-dimethylbutane, 1,4-dibromo-2,2-dimethylbutane, 1,4-dibromo-3-methylpentane, 1,4-dibromo-2,3-dimethylbutane, 1,4-dibromo-2,3-dimethylpentane, 1,4-dibromo-2-(4'-ethylphenyl)butane, 1,4-dibromo-2-(4'-isopropylphenyl)butane, 1,4-dibromo-3-phenyl-butane, 1,4-dibromo-2-phenyl-butane or 4-bromobutyl-1-p-toluene sulfonate.

5. The process of claim 1 wherein the products formed by the process are 6-carboxy-3,4-dihydro-2H-pyran, 6-carboxy-2-methyl-3,4-dihydro-2H-pyran, 6-carboxy-3-methyl-3,4-dihydro-2H-pyran, 6-carboxy-4-methyl-3,4-dihydro-2H-pyran, 6-carboxy-3,3-dimethyl-3,4-dihydro-2H-pyran, 6-carboxy-4,4-dimethyl-3,4-dihydro-2H-pyran, 6-carboxy-2,3-dimethyl-3,4-dihydro-2H-pyran, 6-carboxy-3,4-dimethyl-3,4-dihydro-2H-pyran, 6-carboxy-2,3,4-trimethyl-3,4-dihydro-2H-pyran, 6-carboxy-4-(4'-ethylphenyl)-3,4-dihydro-2H-pyran, 6-carboxy-4-(4'-isopropylphenyl)-3,4-dihydro-2H-pyran, 6-carboxy-3-phenyl-3,4-dihydro-2H-pyran, and 6-carboxy-4-phenyl-3,4-dihydro-2H-pyran.

6. The process of claim 1, wherein the carbon monoxide pressure is from about 300 to 3000 psig.

7. The process of claim 6, wherein the carbon monoxide pressure is from about 500 to 1000 psig.

8. The process of claim 1, wherein the reaction is carried out at a temperature of from about 30° C. to about 150° C.

9. The process of claim 1, wherein the inorganic base is selected from LiOH, NaOH, KOH, RbOH, Ca(OH)$_2$, Ba(OH)$_2$ or Mg(OH)$_2$.

10. The process of claim 1, wherein the molar ratio of the inorganic base is from about 1 to 10 moles per mole of 1,4-disubstituted butane reactant.

11. The process of claim 1, wherein the metal carbonyl catalyst compound is iron pentacarbonyl, dicobalt-octacarbonyl, or nickel-tetracarbonyl.

12. The process of claim 11, wherein the metal carbonyl is dicobalt-octacarbonyl.

13. The process of claim 11, wherein the metal carbonyl catalyst compound is a salt of iron pentacarbonyl, dicobaltoctacarbonyl or nickel-tetracarbonyl.

14. The process of claim 13, wherein said salt is sodium, potassium or calcium salt.

15. The process of claim 1, wherein the catalyst is formed by carbonylation in organic solvent and used in that solvent.

16. The process of claim 1, wherein the molar percentage of metal carbonyl compound to 1,4-disubstituted butane reactant is from about 0.1 to about 25%.

17. The process of claim 1, wherein the liquid solvent medium is a mixture of water and alcohol.

18. The process of claim 17, wherein the mixture consists of from about 10% to about 90% by weight water and from about 90% to about 10% alcohol.

19. The process of claim 17, wherein the alcohol is a saturated, linear or branched, aliphatic, monohydroxylic or polyhydroxylic compound containing up to 6 carbon atoms.

20. The process of claim 19, wherein the alcohol is tert-butanol.

21. The process of claim 19, wherein the alcohol is isopropanol.

* * * * *